United States Patent [19]
Huss, Jr. et al.

[11] Patent Number: 5,489,726
[45] Date of Patent: Feb. 6, 1996

[54] HIGHLY SELECTIVE N-OLEFIN ISOMERIZATION PROCESS USING MULTIPLE PARALLEL REACTORS

[75] Inventors: Albin Huss, Jr., Chadds Ford, Pa.; Iraj I. Rahmim, Voorhees, N.J.; Peter Wood, Buck, England

[73] Assignee: Mobil Oil Corporation, Fairfax, Va.

[21] Appl. No.: 233,164

[22] Filed: Apr. 26, 1994

[51] Int. Cl.$^6$ .............................. C07C 5/22; C07C 5/27
[52] U.S. Cl. .............................................. 585/671
[58] Field of Search ............................................ 585/671

[56] References Cited

U.S. PATENT DOCUMENTS

| | | | |
|---|---|---|---|
| 4,448,673 | 5/1984 | Shihabi | 208/111 |
| 4,487,985 | 12/1984 | Tabak | 585/517 |
| 4,547,602 | 10/1985 | Tabak | 585/314 |
| 4,774,376 | 9/1988 | Hall | 585/312 |
| 4,789,528 | 12/1988 | Owen et al. | 422/190 |
| 4,973,778 | 11/1990 | Harandi et al. | 585/407 |
| 5,227,569 | 7/1993 | O'Young et al. | 585/671 |
| 5,254,789 | 10/1993 | Gajda | 585/671 |

*Primary Examiner*—Asok Pal
*Assistant Examiner*—E. D. Irzinski
*Attorney, Agent, or Firm*—Alexander J. McKillop; Dennis P. Santini; Laurence P. Hobbes

[57] ABSTRACT

A process is disclosed for the continuous highly selective skeletal isomerization of linear olefin-containing organic feeds to iso-olefins over constrained intermediate pore zeolites, e.g., ZSM-35, using multiple parallel reactors.

20 Claims, 2 Drawing Sheets

HIGHLY SELECTIVE N-OLEFIN ISOMERIZATION PROCESS USING MULTIPLE PARALLEL REACTORS

FIELD OF THE INVENTION

This invention relates to a method for the high level catalytic conversion of n-olefin-containing, e.g., n-butene-containing, hydrocarbon streams to iso-olefin-rich, e.g., isobutene-rich product streams under skeletal isomerization conditions using multiple parallel reactors.

BACKGROUND OF THE INVENTION

The demand for iso-alkenes has recently increased. For example, relatively large amounts of isobutene are required for reaction with methanol or ethanol over an acidic catalyst to produce methyl tert-butyl ether (MTBE) or ethyl tert-butyl ether (ETBE) which is useful as an octane enhancer for unleaded gasolines. Isoamylenes are required for reaction with methanol over an acidic catalyst to produce tert-amyl methyl ether (TAME). With passage of the Clean Air Act in the United States mandating increased gasoline oxygenate content, MTBE, ETBE and TAME have taken on new value as clean-air additives, even for lower octane gasolines. Lead phasedown of gasolines in Western Europe has further increased the demand for such oxygenates.

An article by J. D. Chase, et al., *Oil and Gas Journal*, Apr. 9, 1979, discusses the advantages one can achieve by using such materials to enhance gasoline octane. The blending octane values of MTBE when added to a typical unleaded gasoline base fuel are RON=118, MON=101, R+M/2=109. The blending octane values of TAME when added to a typical unleaded gasoline base fuel are RON=112, MON=99, R+M/2=106. Isobutene (or isobutylene) is in particularly high demand as it is reacted with methanol to produce MTBE.

The addition of shape-selective zeolite additives such as ZSM-5 to cracking catalysts, e.g., those used in fluidized catalytic cracking (FCC), is beneficial in producing gasoline boiling range product of increased octane rating. However, increased amounts of olefins result, including n-butenes, creating a need for their conversion to higher value products such as isobutene which can be used to produce MTBE.

Butene exists in four isomers: butene-1, cis-butene-2, its stereo-isomer trans-butene-2, and isobutene. Conversions between the butenes-2 is known as geometric isomerization, whereas that between butene-1 and the butenes-2 is known as position isomerization, double-bond migration, or hydrogen-shift isomerization. The aforementioned three isomers are not branched and are known collectively as normal or n-butenes. Conversion of the n-butenes to isobutene, which is a branched isomer, is widely known as skeletal isomerization.

The reaction of tertiary olefins with alkanol to produce alkyl tertiary alkyl ether is selective with respect to iso-olefins. Linear olefins are unreactive in the acid catalyzed reaction, even to the extent that it is known that the process can be utilized as a method to separate linear and iso-olefins. The typical feedstream of FCC $C_4$ or $C_4$+ crackate used to produce tertiary alkyl ethers in the prior art which contains normal butene and isobutene utilizes only the branched olefin in etherification. This situation presents an exigent challenge to workers in the field to discover a technically and economically practical means to utilize linear olefins, particularly normal butene, in the manufacture of tertiary alkyl ethers.

In recent years, a major development within the petroleum industry has been the discovery of the special catalytic capabilities of a family of zeolite catalysts based upon medium pore size shape selective metallosilicates. Discoveries have been made leading to a series of analogous processes drawn from the catalytic capability of zeolites in the restructuring of olefins.

Despite these efforts, the skeletal isomerization of olefins e.g., to produce isobutene, has been hampered by relatively low conversion and/or selectivity to isobutene perhaps owing to the lability of these olefins. It is further known that skeletal isomerization becomes more difficult as hydrocarbons of lower molecular weight are used, requiring higher temperatures and lower linear olefin partial pressures.

Generally, the conversion of n-butenes to iso-butene is conducted at selectivities below 90%. In order to obtain higher selectivities, operation at high temperatures (>500° C.) and with high feed dilution (butene partial pressure, typically less than 5 psia (34.5 kPa)) is generally required. Selectivities of greater than 85%, 90%, 95% or even 99% are highly advantageous in commercial conversion of n-butenes to isobutene in order to avoid the need to separate out materials other than n-butene from the product stream. Such high selectivities will permit direct (cascading) or indirect introduction of the isomerizer effluent to an etherification zone where isobutene is reacted with alkanol to produce alkyl tert-butyl ether, e.g., MTBE. Unconverted n-butenes in the etherification zone can be withdrawn either before the etherification zone or preferably, from the etherification zone effluent insofar as the etherification reaction utilizes only the isobutene component of the isomerizer stream. Unreacted n-butenes from the etherification zone effluent can be recycled to the isomerizer where they are converted to isobutene at high selectivity. If the recycle stream contains not only unconverted linear olefins, e.g., n-butenes, but also by-products such as other olefins (e.g., propylene) or paraffins, they have to be removed from the recycle stream, such as by distillation or by taking a slip stream. These removal steps are expensive and can lead to considerable loss of not only the by-products but butenes as well. These losses are larger when the by-products formed are present in higher concentration. Thus, even small improvements in the isobutene selectivity during n-butene isomerization have a major effect on the commercial viability of the process.

Further enhancement of total yield of iso-olefin can be effected by enhancing overall conversion of the n-olefin-containing feedstream. With this object in mind, it would be advantageous to provide a skeletal isomerization catalyst capable of maintaining a high level of conversion as well as high iso-olefin selectivity, even at relatively low temperatures, e.g., no greater than 450° C. and high n-olefin space velocities, e.g., no less than 5, e.g., no less than 70. Such catalyst materials include constrained intermediate pore size zeolites.

These zeolites, exemplified by ZSM-22, ZSM-23, and ZSM-35, are members of a unique class of zeolites. They have channels described by 10-membered rings of T (=Si or Al) or oxygen atoms, i.e., they are intermediate pore zeolites, distinct from small pore 8-ring or large pore 12-ring zeolites. They differ, however, from other intermediate pore 10-ring zeolites, such as ZSM-5, ZSM-11, ZSM-57 or stilbite, in having a smaller 10-ring channel. If the crystal structure (and hence pore system) is known, a convenient measure of the channel cross-section is given by the product of the dimensions (in angstrom units) of the two major axes of the pores. These dimensions are listed in the "Atlas of Zeolite Structure Types" by W. M. Meier and D. H. Olson, Butterworths, publisher, Second Edition, 1987. The values of this product, termed the Pore Size Index, are listed in Table A.

TABLE A

Pore Size Index

| Type | Largest Ring Size | Zeolite | Axes of Largest Channel, A | Pore Size Index |
|---|---|---|---|---|
| 1 | 8 | Chabazite | 3.8 × 3.8 | 14.4 |
|  |  | Erionite | 3.6 × 5.1 | 18.4 |
|  |  | Linde A | 4.1 × 4.1 | 16.8 |
| 2 | 10 | ZSM-22 | 4.4 × 5.5 | 24.2 |
|  |  | ZSM-23 | 4.5 × 5.2 | 23.4 |
|  |  | ZSM-35 | 4.2 × 5.4 | 22.7 |
|  |  | ALPO-11 | 3.9 × 6.3 | 24.6 |
| 3 | 10 | ZSM-5 | 5.3 × 5.6 | 29.1 |
|  |  | ZSM-11 | 5.3 × 5.4 | 28.6 |
|  |  | Stilbite | 4.9 × 6.1 | 29.9 |
|  |  | ZSM-57 (10) | 5.1 × 5.8 | 29.6 |
| 4 | 12 | ZSM-12 | 5.5 × 5.9 | 32.4 |
|  |  | Mordenite | 6.5 × 7.0 | 45.5 |
|  |  | Beta (C-56) | 6.2 × 7.7 | 47.7 |
|  |  | Linde-L | 7.1 × 7.1 | 50.4 |
|  |  | Mazzite (ZSM-4) | 7.4 × 7.4 | 54.8 |
|  |  | ALPO$_4$-5 | 7.3 × 7.3 | 53.3 |

It can be seen that small pore, eight-ring zeolites have a Pore Size Index below about 17, the intermediate pore, 10-ring zeolites of about 22–30, and large pore, 12-ring zeolites above about 32. It is also apparent, that the 10-ring zeolites are grouped in two distinct classes; Type 2 with a Pore Size Index between about 22.7 and 24.6, and more broadly between about 20 and 26, and Type 3 with a Pore Size Index between 28.6 and 29.9, or more broadly, between about 28 and 31.

The zeolites useful for this invention are those of Type 2 with a Pore Size Index of 20–26.

Alternatively, these zeolites can be distinguished from Type 1 and Type 3 zeolites by their sorption characteristics. Equilibrium sorption data are listed in Table B below. While both Type 2 and Type 3 zeolites sorb more than about 40 mg n-hexane per gram zeolite, the Type 2 zeolites sorb less than 40 mg 3-methylpentane under the conditions specified, in contrast to Type 3 zeolites. Small pore, 8-ring zeolites sorb less than 15 mg of 3-methylpentane per gram of zeolite.

The equilibrium sorption are obtained most conveniently in a thermogravimetric balance by passing a stream of inert gas such as helium containing the hydrocarbon with the indicated partial pressure over the dried zeolite sample held at 90° C. for a time sufficient to obtain a constant weight.

This method of characterizing the Type 2 zeolites has the advantage that it can be applied to new zeolites whose crystal structure has not yet been determined. For mixtures of zeolites with amorphous material or for poorly crystallized samples, the numbers apply only to the crystalline portion.

Thus, zeolites useful for the present invention sorb 30 to 55 mg n-hexane and 15 to 40 mg 3-methylpentane per g dry zeolite in the hydrogen form.

TABLE B

Equilibrium Sorption Data of Medium Pore Zeolites

| | | Amount sorbed, mg per g zeolite | |
|---|---|---|---|
| Type | Zeolite | n-Hexane[a] | 3-Methylpentane[b] |
| 2 | ZSM-22 | 40 | 20 |
|  | ZSM-23 | 45 | 25 |
|  | ZSM-35 | 50 | 25 |
| 3 | ZSM-5 | 103 | 61 |
|  | ZSM-12 | 52 | 58 |
|  | ZSM-57 | 60 | 70 |

TABLE B-continued

Equilibrium Sorption Data of Medium Pore Zeolites

| | | Amount sorbed, mg per g zeolite | |
|---|---|---|---|
| Type | Zeolite | n-Hexane[a] | 3-Methylpentane[b] |
|  | MCM-22 | 89 | 79 |

[a] at 90° C., 83 torr n-hexane
[b] at 90° C., 90 torr 3-methylpentane

ZSM-22 is more particularly described in U.S. Pat. No. 4,556,477, the entire contents of which are incorporated herein by reference. ZSM-22 and its preparation in microcrystalline form using ethylpyridinium as directing agent are described in U.S. Pat. No. 4,481,177 to Valyocsik, the entire contents of which are incorporated herein by reference. For purposes of the present invention, ZSM-22 is considered to include its isotypes, e.g., Theta-1, Gallo-Theta-1, NU-10, ISI-1, and KZ-2.

ZSM-23 is more particularly described in U.S. Pat. No. 4,076,842, the entire contents of which are incorporated herein by reference. For purposes of the present invention, ZSM-22 is considered to include its isotypes, e.g., EU-13, ISI-4, and KZ-1.

ZSM-35 is more particularly described in U.S. Pat. No. 4,016,245, the entire contents of which are incorporated herein by reference. For purposes of the present invention, ZSM-35 is considered to include its isotypes, e.g., ferrierite, FU-9, ISI-6, NU-23, and Sr-D.

The zeolite catalyst used is preferably at least partly in the hydrogen form, e.g., HZSM-22, HZSM-23, or HZSM-35. Other metals or cations thereof, e.g. rare earth cations, may also be present. When the zeolites are prepared in the presence of organic cations, they may be quite inactive possibly because the intracrystalline free space is occupied by the organic cations from the forming solution. The zeolite may be activated by heating in an inert or oxidative atmosphere to remove the organic cations, e.g. by heating at over 500° C. for 1 hour or more. The hydrogen form can then be obtained by base exchange with ammonium salts followed by calcination, e.g. at 500° C. in air.

Many catalytic conversion processes operate with several reactors rather than only one reactor. Multi-reactor systems can provide greater process control than can be maintained in a single reactor vessel. Moreover, it is often more economical to install several small vessels rather than one very large vessel. Additionally, process flexibility may be increased with multiple reactors so that different operating conditions can be used in each reactor, thus resulting in different product yields, variations in catalyst aging or ultimate life, changes in conversion of feed, or combinations of all of the above.

Multiple reactors may be used in two basic flow configurations. Reactors may be manifolded to operate in parallel or series flow. However, reactors can only be practically used in parallel flow arrangement if the feedstock can be economically converted in a single pass through a catalyst bed. When the catalyst in the reactors requires frequent replacement or reactivation, an extra reactor may be installed and throughput can remain constant during catalyst replacement or reactivation.

Skeletal isomerization operation with the constrained intermediate pore size zeolite catalyst is preferably carried out at relatively high temperatures, e.g., 400° C., and low olefin partial pressures, e.g., 1 atm. Though selectivities for isobutylene are generally high, e.g., greater than 80%, the process can experience relatively low selectivities, e.g., 60%, for the first day or so of operation with fresh or freshly regenerated catalyst on stream.

Accordingly, it would be advantageous to devise an olefin skeletal isomerization process operation whereby the cycle length (time between successive regenerations of catalyst) and catalyst life are increased, while maximizing iso-olefin selectivity during initial operation with fresh or freshly regenerated catalyst.

SUMMARY OF THE INVENTION

It has now been found that continuous olefin skeletal isomerization can be carried out advantageously in a multiple parallel reactor system, wherein single reactor operation at high feed space velocity is alternated with plural reactor operation in parallel at lower feed space velocity. Relatively constant feed throughput and product output as well as high iso-olefin selectivity can be maintained by such operation.

Olefin skeletal isomerization is an equilibrium limited reaction. Low selectivity at early times on stream (TOS) can result from over-conversion. In order to optimize conversion/selectivity performance and cycle length, it is necessary to operate at or below the conversion level required to reach thermodynamic equilibrium iso-olefin/(iso-olefin+n-olefin) ratios (i/i+n). This conversion level will vary with various conditions including feed iso-olefin level, reactor temperature (higher temperatures provide lower equilibrium i/i+n levels), and the carbon number of the feed being processed (i/i+n equilibrium values differ when C4 rather than C5 feed is used). The present invention's use of multiple reactors sequencing allows the avoidance of over-conversion while extending cycle length.

For single reactor operation, the olefin skeletal isomerization catalyst employed is utilized in fresh or freshly regenerated condition. Such a catalyst may contain less than 0.5 wt % coke and can provide a linear butene feed conversion of greater than 30 wt % at conditions which comprise temperatures of less than about 450° C. and feed/catalyst space velocities of 5 $hr^{-1}$ or higher. Because operation with freshly regenerated catalyst can result in low iso-olefin selectivity initially due to over-conversion, it has been found that operation at relatively high feed space velocity is advantageous early after streaming of said catalyst. Single reactor operation is carried out until the linear olefin feed conversion activity is reduced by at least 5%, say, 5 to 30%, preferably 10 to less than 20%, relative to the fresh or freshly regenerated catalyst and the i/i+n selectivity increased by at least 5%, say 5 to 40%, preferably 10 to 30%, relative to the fresh or freshly regenerated catalyst. When the catalyst has met these criteria it is considered selectivated and the feed is directed to another reactor containing fresh or freshly regenerated catalyst.

For present purposes a selectivated catalyst can contain a greater amount of coke than freshly regenerated catalyst. Furthermore, it has been found that once the catalyst has been selectivated, it can be used under conditions similar to those for freshly regenerated catalyst but at a reduced reactor feed space velocity, until the catalyst is at least partially deactivated. In order to provide constant overall throughput during operation with coke-selectivated catalyst, it has been found that operation with plural parallel reactors at reduced reactor throughput per reactor is advantageous to the olefin skeletal isomerization operation, once freshly regenerated catalyst has been selectivated.

Plural reactor operation can also be carried out with one or more reactors containing partially deactivated catalyst, or with at least one reactor containing coke-selectivated catalyst and at least one reactor containing partially deactivated catalyst. Catalyst is considered partially deactivated catalyst when the linear olefin feed conversion activity is reduced by at least 10%, say, 10 to 40%, preferably 20 to less than 30%, relative to the fresh or freshly regenerated catalyst when tested under the same operating conditions.

Once the catalyst in a reactor reaches a deactivated condition, the reactor is taken out of service until the catalyst is regenerated. For present purposes, catalyst is considered deactivated catalyst when the linear olefin feed conversion activity is reduced by at least 15%, say, 15 to 50%, preferably 30 to 40%, relative to the fresh or freshly regenerated catalyst.

Accordingly, the present invention relates to a continuous process for olefin skeletal isomerization of linear olefins to iso-olefins by contacting a linear olefin-containing feed under olefin skeletal isomerization conditions, with an olefin skeletal isomerization catalyst showing both a loss in conversion activity on aging and improvement in iso-olefin selectivity on aging. High iso-olefin selectivity and long catalyst life is obtained by operating a plural parallel reactor system in a process comprising:

a) isomerizing olefins at a high space velocity by directing a portion of said feed in single reactor operation, i.e., one reactor in isomerizing operation at any given time, seriatim to a plurality of reactors containing freshly regenerated catalyst at a determinable feed space velocity and withdrawing iso-olefin rich product, said feed being directed to a succeeding reactor when the conversion activity of said catalyst in the reactor previous thereto is reduced by a predetermined amount to selectivate the catalyst, i.e., to enhance the iso-olefin selectivity of the catalyst relative to fresh or freshly regenerated catalyst, until the conversion activity of the catalyst has been so selectivated in a plurality of reactors, while optionally simultaneously regenerating any deactivated olefin skeletal isomerization catalyst in reactors not in isomerization operation;

b) isomerizing olefins with selectivated catalyst by directing another portion of said feed to a plurality of said reactors operating in parallel, containing selectivated catalyst, wherein the space velocity for each reactor is reduced by at least 25% relative to the single reactor operation of step a), until at least one of said reactors contains catalyst whose conversion activity has been reduced by a predetermined amount to a deactivated condition, withdrawing iso-olefin rich product, and optionally simultaneously regenerating any deactivated olefin skeletal isomerization catalyst in reactors not in isomerization operation; and c) repeating steps a) and b).

Alternatively, the present invention can be described as a continuous process for olefin skeletal isomerization of linear olefins to iso-olefins by contacting a linear olefin-containing feed, e.g., linear butene-containing or linear pentene-containing feeds, under olefin skeletal isomerization conditions, with an olefin skeletal isomerization catalyst, comprising a zeolite having the structure selected from the group consisting of ZSM-22, ZSM-23, and ZSM-35, showing both a loss in conversion activity on aging and improvement in iso-olefin selectivity on aging, whereby high iso-olefin selectivity and long catalyst life is obtained which comprises operation of a plural parallel reactor system, e.g., one having a first reactor, a second reactor and a third reactor, said process comprising:

a) isomerizing olefins at a high space velocity in single reactor operation by directing a portion of said feed to a reactor containing freshly regenerated catalyst and withdrawing iso-olefin rich product, until the conversion activity of the catalyst has been reduced by a predetermined amount to selectivate said catalyst therein and directing another portion of said feed to another single reactor until the conversion activity of the catalyst has been reduced by a predetermined amount to selectivate said catalyst therein until at least a plurality of said reactors contain selectivated catalyst, and optionally simultaneously regenerating any deactivated catalyst in reactors not in isomerization operation;

b) isomerizing olefins with selectivated catalyst by simultaneously directing another portion of said feed to a plurality of said reactors operating in parallel, containing selectivated catalyst, wherein the space velocity for each reactor is reduced by at least 25% relative to the single reactor operation of step a), until at least one of said reactors contains catalyst whose conversion activity has been reduced by a predetermined amount to a deactivated condition, withdrawing iso-olefin rich product, and optionally simultaneously regenerating any deactivated olefin skeletal isomerization catalyst in reactors not in isomerization operation; and c) repeating steps a) and b).

DETAILED DESCRIPTION OF THE INVENTION

The present invention provides a process which converts a linear olefin-containing hydrocarbon feedstream to an iso-olefin rich product at high levels of conversion and high iso-olefin selectivity over a constrained intermediate pore size zeolite catalyst, e.g., material having the structure selected from the group consisting of ZSM-22, ZSM-23, and ZSM-35, in a multiple parallel reactor system.

The skeletal isomerization reaction of the present invention is carried out at temperatures between 100° and 750° C.; weight hourly space velocity based on linear olefin in the feed between 0.1 and 500 WHSV; and linear olefin partial pressure between 2 and 2000 kPa. The preferred conditions are temperatures between 150° and 600° C., more preferably between 200° and 550° C., WHSV between 0.5 and 400, more preferably between 1 and 100; and a linear olefin partial pressure between 10 and 500 kPa, more preferably between 20 and 200 kPa. Under these conditions the conversion of linear olefin, e.g., n-butene, can be at least 20%, preferably at least 35% and more preferably at least 45%. The selectivity to iso-olefin, e.g., isobutene, is at least 75%, preferably at least 85%, 90%, or even 95%. In the case of pentenes conversion, conversions over 65% are typical.

The present invention is especially suited to processes carried out at high linear olefin to iso-olefin selectivity, e.g., at least 60% at relatively low conversion temperatures and high linear olefin partial pressures. Such processes can maintain selectivities of at least 75, 85 or 95% at a conversion temperature less than or equal to: 550°, 450°, 400° or even 350° C., and linear olefin partial pressures above 2 psia (14 kPa), e.g., above 5 psia (34 kPa). Such processes can be carried out at an overall conversion of linear olefins of at least 15, 30, 35, 40, or 45 wt % or higher. The present method is particularly effective when operating at lower temperatures, e.g., less than 450° C. and at relatively high WHSV, e.g., no less than 1, 5, or even 20.

Preferred feedstreams for use in the present invention include $C_4$ or $C_4+$ hydrocarbon feedstreams, e.g., C5 or C5+ hydrocarbon feedstreams. Linear olefins suited to use in the present invention may be derived from a fresh feedstream, preferably comprising n-butenes and/or n-pentenes, or from the effluent of an iso-olefin etherification reactor which employs alkanol and $C_4$ or $C_4+$ hydrocarbon feedstock. Typical hydrocarbon feedstock materials for isomerization reactions according to the present invention include olefinic streams, such as cracking process light gas containing butene isomers in mixture with substantial amounts of paraffins including n-butane and isobutane. The $C_4$ components usually contain a major amount of unsaturated compounds, such as 10–40% isobutene, 20–55% linear butenes, and small amounts of butadiene. Also, $C_4+$ heavier olefinic hydrocarbon streams may be used, e.g., $C_4$ to $C_{10}$, preferably $C_4$ to $C_6$ olefinic hydrocarbon streams, e.g., light FCC gasoline. Feedstocks comprising at least 5 wt % n-butenes or n-pentenes can be used in the present method.

Operation with constrained intermediate pore size zeolite is carried out under relatively high temperatures and low olefin partial pressures. Although selectivities for isobutene are generally high, e.g., greater than 80%, the process can experience relatively low selectivities, e.g., 60% for the first day or so of fresh or freshly regenerated catalyst on stream.

The zeolite catalyst used is preferably at least partly in the hydrogen form, e.g., HZSM-35, but other cations, e.g., rare earth cations, may also be present. When the zeolites are prepared in the presence of organic cations, they may be quite inactive possibly because the intracrystalline free space is occupied by the organic cations from the forming solution. The zeolite may be activated by heating in an inert atmosphere to remove the organic cations e.g., by heating at over 500° C. for 1 hour or more. The hydrogen form can then be obtained by base exchange with ammonium salts followed by calcination e.g., at 500° C. in air. Other cations, e.g., metal cations, can be introduced by conventional base exchange or impregnation techniques.

The zeolite, e.g., ZSM-22, ZSM-23, or ZSM-35, may be incorporated in another material usually referred to as a matrix or binder. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

Of all the foregoing materials, silica may be preferred as the matrix material owing to its relative inertness for catalytic polymerization and cracking reactions which are preferably minimized in the instant isomerization processes. Alternatively, silica-containing matrix containing a minor amount of aluminum may be employed. The relative proportions of finely divided ZSM-35 and inorganic oxide gel matrix vary widely with the zeolite content ranging from about 1 to about 90 percent by weight and more usually in the range of about 30 to about 80 percent by weight of the composite.

The regeneration of spent zeolite catalyst used in the isomerization reaction is carried out oxidatively or hydrogenatively employing procedures known in the art. The catalyst of the present invention can be readily reactivated without significantly reducing selectivity for isobutene by exposing it to hydrogen for a suitable period, e.g., overnight.

In order to obtain desired linear olefin skeletal isomerization activity/selectivity, ZSM-35, preferably in the hydrogen form, should have an alpha value of at least 2, preferably at least 10 when used in the catalyst of the present invention. Alpha value, or alpha number, of a zeolite is a measure of zeolite acidic functionality and is more fully described together with details of its measurement in U.S. Pat. No. 4,016,218, *J. Catalysis,* 6, pp. 278–287 (1966) and *J. Catalysis,* 61, pp. 390–396 (1980). The experimental conditions cited in the latter reference are used for characterizing the catalysts described herein.

SKELETAL ISOMERIZATION PROCESS

Single Reactor Operation

Figure 1:
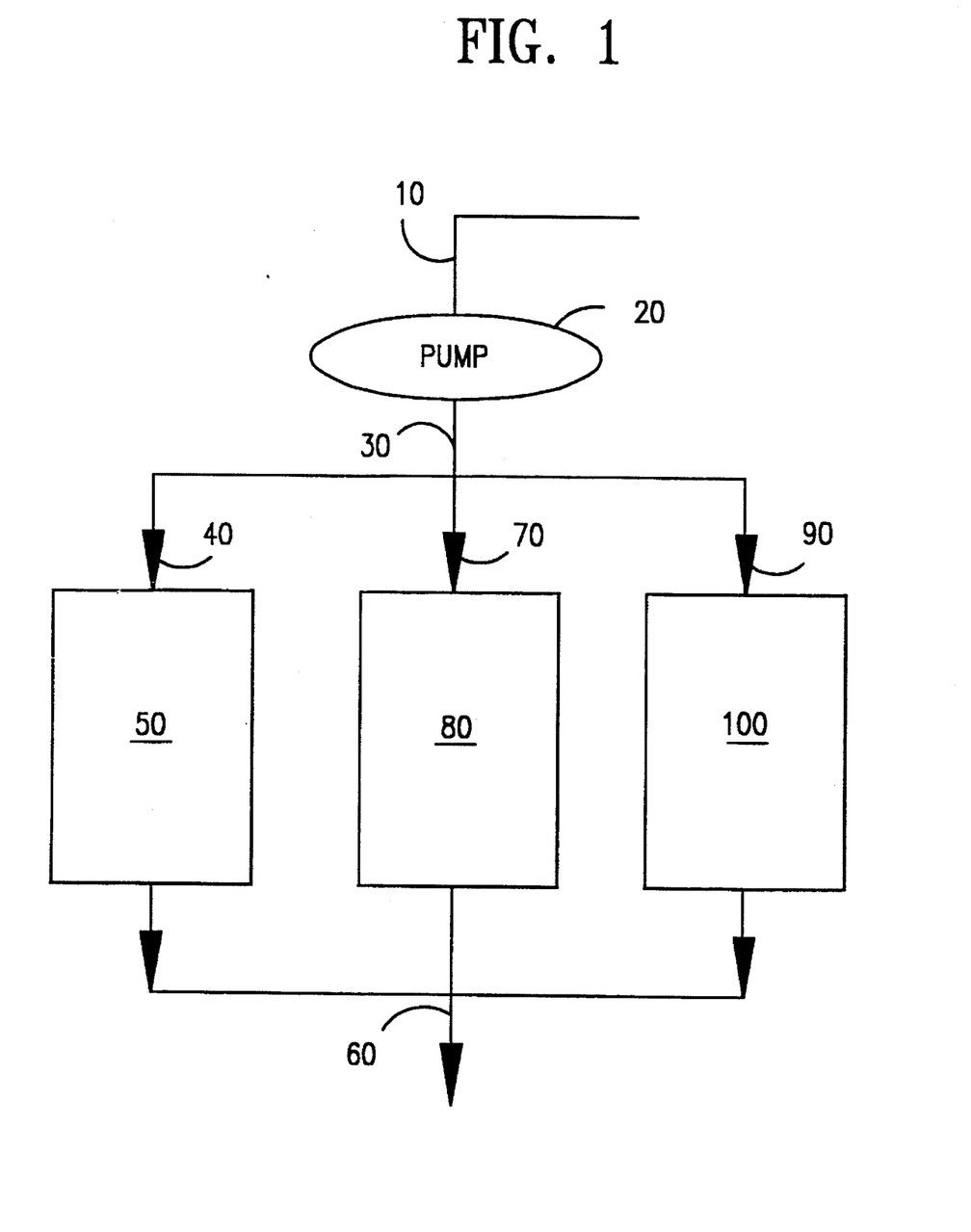
FIG. 1 depicts a multiple parallel reactor configuration for an isomerization process of the present invention, employing three reactors in parallel.

Referring to the drawing of FIG. 1, the flow sheet shows a preferred process employing multiple parallel reactors wherein the total olefinic feedstock 10 is passed to a pump 20 which is used to feed three reactors in parallel (where valves can be used to direct the feed toward one, two, or all three reactors). The feedstock is passed from the pump 20 at a fixed feed rate through line 30 through open valve 40 to a first isomerization reactor 50 which is maintained under single reactor isomerization conditions and which contains fresh or freshly regenerated ZSM-35 catalyst. Here the linear olefin-containing feed is converted to an iso-olefin rich product. The iso-olefin rich reactor effluent is then withdrawn through line 60 where it is collected or further processed, e.g., by etherification of iso-olefin with alkanol. The isomerization is carried out in said reactor 50 until the catalyst is selectivated. At this point, valve 40 is closed and feed 30 is directed through open valve 70 to a second isomerization reactor 80 which is maintained under single reactor isomerization conditions which contains fresh or freshly regenerated ZSM-35 catalyst. The linear olefin-containing feed is converted to an iso-olefin rich product and the reactor effluent is then withdrawn through line 60. Isomerization is carried out in said reactor 80 until the catalyst is selectivated. At this point, valve 70 is closed and feed 30 is directed through open valve 90 to a third isomerization reactor 100 which is maintained under single reactor isomerization conditions and which also contains fresh or freshly regenerated ZSM-35 catalyst. The linear olefin-containing feed is converted to an iso-olefin rich product and the reactor effluent is then withdrawn through line 60. Isomerization is carried out in said reactor 100 until the catalyst is selectivated. At this point, the three reactor system comprises three reactors which contain selectivated catalyst.

Dual Reactor Parallel Operation

At this point, valves 40 and 70 are opened and olefinic feedstock 10 is passed to a pump 20 and thence at the same fixed total feed rate through line 30 through open valves 40 and 70 to the first isomerization reactor 50 and second isomerization reactor 80 which are maintained under dual reactor isomerization conditions, i.e., the feed space velocities through the two reactors are reduced by one-half relative to single reactor operation (while maintaining overall throughput). The linear olefin-containing feed is converted to an iso-olefin rich product and the iso-olefin rich reactor effluent from both reactors is then withdrawn through line 60 where it can be further processed. The isomerization is carried out in said reactors 50 and 80 until a point before which the catalyst therein is partially deactivated.

Valve 70 is then closed and feed 30 is directed through open valves 40 and 90 to the first and third isomerization reactors 50 and 100 in parallel which are maintained under dual reactor isomerization conditions similar to the dual reactor operation described above. The isomerization is carried out in said reactor 50 (containing partially deactivated catalyst) and reactor 100 (containing selectivated catalyst) until the catalyst in reactor 50 is deactivated and the catalyst in reactor 100 is partially deactivated.

Valve 40 is then closed and feed 30 is directed through open valves 70 and 90 to the second and third isomerization reactors 80 and 100 in parallel which are maintained under dual reactor isomerization conditions similar to the dual reactor operations described above. The isomerization is carried out in said reactors 80 and 100 (both containing partially deactivated catalyst) until the catalyst in both reactors is fully deactivated. Simultaneous to the dual operation of the second and third reactors, the first reactor is subjected to catalyst regeneration conditions, e.g., 500° C., 1% $O_2$ in $N_2$, until the catalyst is suitably regenerated.

Single Reactor Operation With Regeneration

Valves 70 and 90 are then closed and feed 30 is directed through open valve 40 to the first isomerization reactor 50 which is maintained under single reactor isomerization conditions and which contains freshly regenerated ZSM-35 catalyst from the regeneration step above. The iso-olefin rich reactor effluent is then withdrawn through line 60 for further processing. The isomerization is carried out in said reactor 50 until the catalyst is selectivated. Simultaneously, the second reactor 80 is subjected to catalyst regeneration conditions, until the catalyst therein is suitably regenerated.

At this point, valve 40 is closed and feed 30 is directed through open valve 70 to the second isomerization reactor 80 which is maintained under single reactor isomerization conditions and which contains freshly regenerated ZSM-35 catalyst from the immediately previous step. The linear olefin-containing feed is converted to an iso-olefin rich product and the reactor effluent is then withdrawn through line 60. Isomerization is carried out in said reactor 80 until the catalyst is selectivated. Simultaneously, the third reactor 100 is subjected to catalyst regeneration conditions, until the catalyst therein is suitably regenerated.

At this point, valve 70 is closed and feed 30 is directed through open valve 90 to the third isomerization reactor 100 which is maintained under single reactor isomerization conditions and which contains freshly regenerated ZSM-35 catalyst from the immediately previous step. The linear olefin-containing feed is converted to an iso-olefin rich product and the reactor effluent is then withdrawn through line 60. Isomerization is carried out in said reactor 100 until the catalyst is selectivated.

Dual reactor parallel operation is then carried out as noted above, followed by single reactor operation with regeneration as just described, followed by said dual reactor parallel operation, etc. thereby providing a continuous process at constant throughput with relatively level selectivity, while enhancing catalyst cycle length and improving selectivities during initial operation with freshly regenerated catalyst. The Table below sets out the above-described reactor configuration/procedure scheme in further detail.

TABLE C

| Reactor on Stream | Reactor on Regen | WHSV in Reactor | Est. Stage Duration (days) | Cumulative Olefin Thpt. (g/g cat) |
|---|---|---|---|---|
| 1 | | 10 | 10 | 800 |
| 2 | | 10 | 10 | 1600 |
| 3 | | 10 | 10 | 2400 |
| 1 & 2 | | 5 | 8 | 3040 |
| 1 & 3 | | 5 | 8 | 3680 |
| 2 & 3 | 1 | 5 | 9 | 4400 |
| 1 | 2 | | | |
| 2 | 3 | | | |
| 3 | | | | |
| 1 & 2 | | | | |
| 1 & 3 | | | | |
| 2 & 3 | 1 | | | |

As is seen from Table C, cycle length (time between successive regenerations) is increased from a typical 10–20 days to nearly 50 days with a corresponding increase in the cumulative olefin throughput during the cycle from an expected 1000–2000 to 4000–5000 grams of olefin processed per gram of catalyst.

Figure 2:
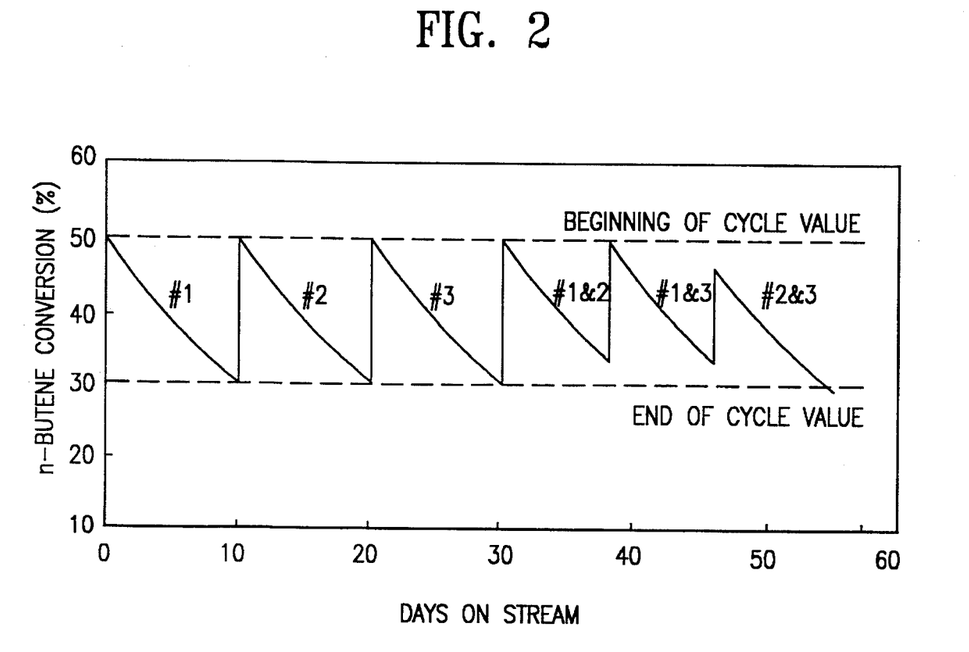
FIG. 2 depicts estimated n-butene conversions to isobutylene for serial single reactor (1,2,3) and serial dual reactor (1&2,1&3,2&3) operation for a three reactor configuration over about 60 days.

FIG. 2 is a graphic plot qualitatively depicting a predicted outcome for linear olefin conversion (wt %) versus days on stream for a three reactor system employing the sequencing of isomerization reactors described above. The graph shows operation wherein single reactor operation (at high WHSV) is carried out to the extent that linear olefin conversion is reduced from 50 wt % to 30 wt % end of cycle conversion. Dual reactor operation (at reduced reactor WHSV) wherein both reactors contain selectivated catalyst is initiated at a beginning of cycle value of 50 wt % linear olefin conversion until an end of cycle value of about 34 wt % conversion is reached. Dual reactor operation (at reduced reactor WHSV) using a reactor with selectivated catalyst and a reactor with partially deactivated catalyst is initiated at a beginning of cycle value of 50 wt % linear olefin conversion until an end of cycle value of about 34 wt % conversion is reached. This is followed by dual reactor operation (at reduced reactor WHSV) wherein both reactors contain partially deactivated catalyst initiated at a beginning of cycle value of 46 wt % linear olefin conversion until an end of cycle value of about 29 wt % conversion is reached. It is seen that single reactor operation with fresh catalyst provides a catalyst cycle of about 10 days on stream until end of cycle conversion value (30% linear olefin conversion) is reached. Dual reactor operation with both reactors containing selectivated catalyst (obtained from single reactor operation) provides a catalyst cycle of about 8 days on stream until end of cycle conversion (33% linear olefin conversion) is reached. Dual reactor operation with a reactor containing selectivated catalyst and a reactor containing partially deactivated catalyst also provides a catalyst cycle of about 8 days. Dual reactor operation with both reactors containing partially deactivated catalyst starting at initial linear olefin conversion of about 45% and ends at about 30% over a 9 day period.

The Example which follows illustrates the invention without restricting it in any way.

EXAMPLE

Figure 3:
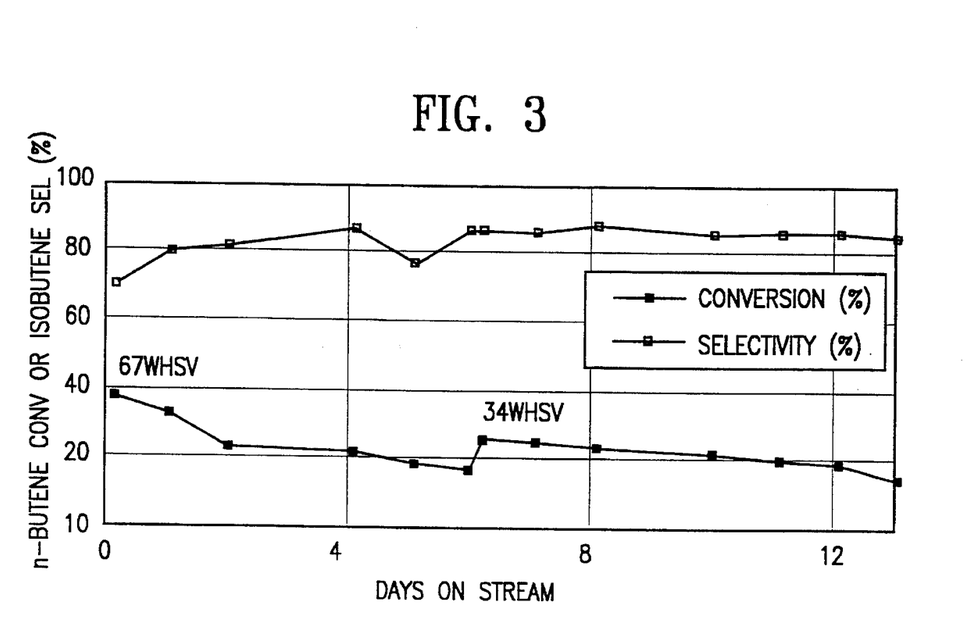
FIG. 3 depicts a simulated multi-reactor olefin skeletal isomerization multi-space velocity operation in a simulated multi-reactor by plotting n-butene conversion and isobutylene selectivity over about 13 days wherein space velocity is decreased from 44 WHSV to 22 WHSV based on C4 olefins on total catalyst after about 6 days on stream.

A ZSM-35 catalyst (65% zeolite, 35% silica, 1/20" quadrulobe extrudate) was accelerated aged at 400° C., 30 psia, using 1/1 vol/vol 1-butene/nitrogen feed. The fresh catalyst was initially streamed at 67 1-butene WHSV on zeolite crystal and after a period of about 6 days on stream, space velocity was dropped to 34 in order to simulate switching from a single reactor at higher. WHSV to two parallel ones at half of the original WHSV. Results are depicted in FIG. 3 which is a graph comparing conversion and selectivity versus days on stream. The simulated sequencing procedure nearly doubled cycle length from 6 days on stream to over 12 days on stream. Further, initial selectivity with the fresh catalyst was significantly better starting at 67 WHSV than what would have been obtained at 34 WHSV.

While the instant invention has been described by specific examples and embodiments, there is no intent to limit the inventive concept except as set forth in the following claims.

What is claimed is:

1. A continuous process for olefin skeletal isomerization of linear olefins to iso-olefins by contacting a linear olefin-containing feed under olefin skeletal isomerization conditions, with an olefin skeletal isomerization catalyst which process comprises operation of a plural parallel reactor system comprising:

a) isomerizing olefins at a weight hourly space velocity between 0.1 and 500 based on linear olefins in the feed by directing a portion of said feed among a plurality of reactors in single reactor operation containing freshly regenerated catalyst having a conversion activity in terms of alpha value of at least 2 and withdrawing product thereby reducing the conversion activity of said catalyst and selectivating said catalyst, directing said feed to a succeeding reactor thereby selectivating said catalyst in the reactor previous thereto, until the catalyst has been so selectivated in a plurality of reactors, while optionally simultaneously regenerating any deactivated olefin skeletal isomerization catalyst in reactors not in isomerization operation;

b) isomerizing olefins with selectivated catalyst by directing another portion of said feed to a plurality of said reactors operating in parallel, containing selectivated catalyst, thereby reducing the weight hourly space velocity for each reactor by at least 25% relative to the single reactor operation of step a), until at least one of said reactors contains catalyst whose conversion activity has been reduced to a deactivated condition, withdrawing product, and optionally simultaneously regenerating any deactivated olefin skeletal isomerization catalyst in reactors not in isomerization operation; and c) repeating steps a) and b).

2. The process of claim 1 wherein said olefin skeletal isomerization catalyst comprises a zeolite selected from the group consisting of ZSM-22, ZSM-23 and ZSM-35, said olefin skeletal isomerization conditions comprise temperatures between about 100° and 750° C., and linear olefin partial pressures between 2 and 2000 kPa, and wherein the space velocity for each reactor in step b) is reduced by at least 50% relative to the single reactor operation of step a).

3. The process of claim 2 wherein said olefin skeletal isomerization conditions comprise temperatures between about 150° and 600° C., weight hourly space velocities based on linear olefins in said feedstock between 0.5 and 400, and linear olefin partial pressures between 10 and 500 kPa.

4. The process of claim 3 wherein said zeolite is ZSM-35 and said olefin skeletal isomerization conditions comprise temperatures between about 200° and 550° C., weight hourly space velocities based on linear olefins in said feedstock between 1 and 100, and linear olefin partial pressures between 20 and 200 kPa.

5. The process of claim 4 further comprising operating said plurality of said reactors operating in parallel of step b) in combinations of two reactors.

6. The process of claim 5 wherein said parallel reactor system comprises a first reactor, a second reactor, and a third reactor.

7. The process of claim 6 further comprising carrying out said isomerizing in step b) in the order: first and second reactors, first and third reactors, and second and third reactors.

8. The process of claim 1 further comprising maintaining a constant overall feed throughput for both steps a) and b).

9. The process of claim 1 further comprising carrying out said regenerating at conditions comprising temperatures of 300° to 650° C.

10. The process of claim 2 wherein said weight hourly space velocity based on linear olefins and zeolite crystal is at least 20 for step a).

11. A continuous process for olefin skeletal isomerization of linear olefins to iso-olefins by contacting a linear butane-containing feed under olefin skeletal isomerization conditions, with an olefin skeletal isomerization catalyst comprising ZSM-35, which comprises operation of a plural parallel reactor system, said process comprising:

a) isomerizing olefins at a weight hourly space velocity between 0.1 and 500 based on linear olefins in the feed in single reactor operation by directing a portion of said feed to a reactor containing freshly regenerated catalyst having a conversion activity in terms of alpha value of at least 2 and withdrawing iso-olefin rich product, thereby reducing the conversion activity of said catalyst and thereby selectivating said catalyst therein and directing another portion of said feed to another single reactor thereby selectivating said catalyst therein until at least a plurality of said reactors contain selectivated catalyst, and optionally simultaneously regenerating any deactivated catalyst in reactors not in isomerization operation;

b) isomerizing olefins with selectivated catalyst by directing another portion of said feed to a plurality of said reactors simultaneously operating in parallel, containing selectivated catalyst, thereby reducing the weight hourly space velocity for each reactor by at least 25% relative to the single reactor operation of step a), until at least one of said reactors contains catalyst whose conversion activity has been reduced to a deactivated condition, withdrawing product, and optionally simultaneously regenerating any deactivated olefin skeletal isomerization catalyst in reactors not in isomerization operation; and c) repeating steps a) and b).

12. The process of claim 11 wherein said olefin skeletal isomerization conditions comprise temperatures between about 100° and 750° C., and linear olefin partial pressures between 2 and 2000 kPa, and wherein the space velocity for each reactor in step b) is reduced by at least 50% relative to the single reactor operation of step a).

13. The process of claim 12 wherein said olefin skeletal isomerization conditions comprise temperatures between about 150° and 600° C., weight hourly space velocities based on linear olefins in said feedstock between 0.5 and 400, and linear olefin partial pressures between 10 and 500 kPa.

14. The process of claim 13 wherein said olefin skeletal isomerization conditions comprise temperatures between about 200° and 550° C., weight hourly space velocities based on linear olefins in said feedstock between 1 and 100, and linear olefin partial pressures between 20 and 200 kPa.

15. The process of claim 14 further comprising operating said plurality of said reactors operating in parallel of step b) in combinations of two reactors.

16. The process of claim 15 wherein said parallel reactor system comprises a first reactor, a second reactor, and a third reactor.

17. The process of claim 16 further comprising carrying out said isomerizing in step b) in the order: first and second reactors, first and third reactors, and second and third reactors.

18. The process of claim 11 wherein the feed for single reactor isomerization in step a) is introduced at the same space velocity as the overall feed space velocity for the plural reactor isomerization in step b).

19. The process of claim 11 further comprising carrying out said regenerating at conditions comprising temperatures of 300° to 650° C.

20. A continuous process for olefin skeletal isomerization of linear olefins to iso-olefins by contacting a linear butene and/or linear pentene-containing feed under olefin skeletal isomerization conditions, with an olefin skeletal isomerization catalyst, comprising ZSM-35, which comprises operation of a plural parallel reactor system having a first reactor, a second reactor and a third reactor, said process comprising:

a) isomerizing olefins at a weight hourly space velocity between 0.1 and 500 based on linear olefins in the feed in single reactor operation by directing a portion of said feed to a reactor containing freshly regenerated catalyst having a conversion activity in terms of alpha value of at least 2 and withdrawing product, thereby reducing the conversion activity of the catalyst and thereby selectivating said catalyst therein and directing another portion of said feed to another single reactor thereby selectivating said catalyst therein until at least a plurality of said reactors contain selectivated catalyst, and optionally simultaneously regenerating any deactivated catalyst in reactors not in isomerization operation;

b) isomerizing olefins with selectivated catalyst by directing another portion of said feed to a plurality of said reactors simultaneously operating in parallel, containing selectivated catalyst, wherein the weight hourly space velocity for each reactor is reduced by at least 25% relative to the single reactor operation of step a), until at least one of said reactors contains catalyst whose conversion activity has been reduced to a deactivated condition, withdrawing product, and optionally simultaneously regenerating any deactivated olefin skeletal isomerization catalyst in reactors not in isomerization operation; and c) repeating steps a) and b).

* * * * *

UNITED STATES PATENT AND TRADEMARK OFFICE
CERTIFICATE OF CORRECTION

PATENT NO. : 5,489,726
DATED : February 6, 1996
INVENTOR(S) : Albin Huss, Jr., et al.

It is certified that error appears in the above-indentified patent and that said Letters Patent is hereby corrected as shown below:

On the title page, item [73],
Assignee should read --Mobil Oil Corporation and BP America Inc.--

Signed and Sealed this

Twenty-ninth Day of October 1996

Attest:

BRUCE LEHMAN

*Attesting Officer*     *Commissioner of Patents and Trademarks*